(12) United States Patent
Gillen et al.

(10) Patent No.: US 7,301,338 B2
(45) Date of Patent: Nov. 27, 2007

(54) AUTOMATIC ADJUSTMENT OF NMR PULSE SEQUENCE TO OPTIMIZE SNR BASED ON REAL TIME ANALYSIS

(75) Inventors: Mike Gillen, The Woodlands, TX (US);
Ole G. Engels, Abu Dhabi (AE); W. Allen Gilchrist, Houston, TX (US);
Darryl E. Trcka, Houston, TX (US);
Thomas Kruspe, Wienhausen (DE);
Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 155 days.

(21) Appl. No.: 11/179,990

(22) Filed: Jul. 12, 2005

(65) Prior Publication Data

US 2005/0257610 A1  Nov. 24, 2005

Related U.S. Application Data

(63) Continuation-in-part of application No. 10/819,665, filed on Apr. 7, 2004, now Pat. No. 7,117,733, and a continuation-in-part of application No. 10/828,812, filed on Apr. 21, 2004, now Pat. No. 7,193,414, which is a continuation of application No. 09/928,768, filed on Aug. 13, 2001, now Pat. No. 6,727,696.

(51) Int. Cl.
*G01V 3/00* (2006.01)
*G01V 3/18* (2006.01)

(52) U.S. Cl. .................. 324/303; 73/152.02

(58) Field of Classification Search .......... 73/152.02; 324/303; 702/8
See application file for complete search history.

(56) References Cited

U.S. PATENT DOCUMENTS

| | | | |
|---|---|---|---|
| 4,646,018 A | 2/1987 | Brown | 324/303 |
| 4,953,399 A | 9/1990 | Fertl et al. | 73/152 |
| 5,023,551 A | 6/1991 | Kleinberg et al. | 324/303 |
| 5,280,243 A * | 1/1994 | Miller | 324/303 |
| 5,309,098 A | 5/1994 | Coates et al. | 324/303 |

(Continued)

FOREIGN PATENT DOCUMENTS

| EP | 0726458 A2 | 8/1996 |
|---|---|---|
| WO | WO01/13142 | 2/2001 |

OTHER PUBLICATIONS

PC AI—Expert Systems, http://www.pcai.com/web/ai info/expert systems.html, pp. 1-15.
What is SNNS? Download from SNNS website.
Frederick Hayes-Roth; *The Knowledge-Based Expert System: A Tutorial*, IEEE Computer 17(9): 11-28, 1984.

*Primary Examiner*—Hezron Williams
*Assistant Examiner*—John Fitzgerald
(74) *Attorney, Agent, or Firm*—Madan, Mossman & Sriram, P.C.

(57) ABSTRACT

Data from a string of multiple formation evaluation data sensor are evaluated by an expert system. Based on the analysis, the logging speed is increased if all the sensors justify it, and is reduced if any of the sensors require a reduced logging speed. Alternatively, the sensitive volume of a NMR sensor is altered based on a determination of a fraction of the sensitive volume that includes a borehole fluid.

14 Claims, 6 Drawing Sheets

U.S. PATENT DOCUMENTS

| | | | |
|---|---|---|---|
| 5,381,092 A | 1/1995 | Freedman | 324/303 |
| 5,486,762 A | 1/1996 | Freedman et al. | 324/303 |
| 5,585,720 A | 12/1996 | Edwards | 324/309 |
| 5,596,191 A | 1/1997 | Mickael | 250/269.4 |
| 5,629,623 A | 5/1997 | Sezginer et al. | 324/303 |
| 5,705,927 A | 1/1998 | Sezginer et al. | 324/303 |
| 5,712,566 A * | 1/1998 | Taicher et al. | 324/303 |
| 5,812,068 A * | 9/1998 | Wisler et al. | 340/855.5 |
| 5,828,214 A * | 10/1998 | Taicher et al. | 324/303 |
| 5,842,149 A | 11/1998 | Harrell et al. | 702/9 |
| 5,936,405 A | 8/1999 | Prammer et al. | 324/303 |
| 6,018,243 A * | 1/2000 | Taicher et al. | 324/303 |
| 6,107,796 A | 8/2000 | Prammer | 324/303 |
| 6,114,851 A | 9/2000 | Kruspe et al. | 324/303 |
| 6,163,153 A | 12/2000 | Reiderman et al. | 324/314 |
| 6,218,833 B1 | 4/2001 | Kruspe et al. | 324/303 |
| 6,366,089 B1 | 4/2002 | Poitzsch et al. | 324/303 |
| 6,373,248 B1 | 4/2002 | Poitzsch et al. | 324/303 |
| 6,603,310 B2 * | 8/2003 | Georgi et al. | 324/303 |
| 6,727,696 B2 * | 4/2004 | Kruspe et al. | 324/303 |
| 6,755,246 B2 * | 6/2004 | Chen et al. | 166/250.01 |
| 6,956,372 B2 * | 10/2005 | Masak et al. | 324/303 |
| 7,032,661 B2 * | 4/2006 | Georgi et al. | 166/250.01 |
| 7,117,733 B2 * | 10/2006 | Engels et al. | 73/152.02 |
| 2003/0128032 A1 | 7/2003 | Heaton et al. | 324/303 |
| 2004/0251898 A1 | 12/2004 | Morys et al. | 324/303 |
| 2005/0017716 A1 | 1/2005 | Fiat | 324/307 |
| 2005/0156592 A1 | 7/2005 | Bordon et al. | 324/303 |
| 2005/0189942 A1 | 9/2005 | Tsao et al. | 324/310 |
| 2005/0257610 A1 | 11/2005 | Gillen et al. | 73/152.02 |
| 2005/0275402 A1 | 12/2005 | Campagna | 324/309 |

* cited by examiner

AUTOMATIC ADJUSTMENT OF NMR PULSE SEQUENCE TO OPTIMIZE SNR BASED ON REAL TIME ANALYSIS

CROSS REFERENCES TO RELATED APPLICATIONS

This application is a continuation-in-part of U.S. patent application Ser. No. 10/819,665 filed on Apr. 7, 2004 now U.S. Pat. No. 7,117,733. This application is also a continuation-in-part of U.S. patent application Ser. No. 10/828,812 filed on Apr. 21, 2004 now U.S. Pat. No. 7,193,414 which is a continuation of U.S. patent application Ser. No. 09/928,768 filed on Aug. 13, 2001 which has issued as U.S. Pat. No. 6,727,696.

FIELD OF THE INVENTION

This invention relates generally to methods of improved logging using oilfield borehole tools and more particularly to dynamic adjustment of the logging speed and acquisition parameters based on the quality of the acquired data and the formations being evaluated.

BACKGROUND OF THE ART

Oil or gas wells are often surveyed to determine one or more geological, petrophysical, geophysical, and well production properties ("parameters of interest") using electronic measuring instruments conveyed into the borehole by an umbilical such as a cable, a wireline, slickline, drill pipe or coiled tubing. Tools adapted to perform such surveys are commonly referred to as formation evaluation tools. These tools use electrical, acoustical, nuclear and/or magnetic energy to stimulate the formations and fluids within the borehole and measure the response of the formations and fluids. The measurements made by downhole instruments are transmitted back to the surface. In many instances, multiple trips or logging runs are needed to collect the necessary data. Additionally, the logging speed is usually a predetermined fixed quantity.

In order to reduce the amount of rig time needed for wireline logging, it is common practice to run multiple sensors in a single run. FOCUS™, from Baker Atlas Inc., is an open hole logging systems suitable for use with the present invention. All of the downhole instruments have been redesigned, incorporating advanced downhole sensor technology, into shorter, lighter, more reliable logging instruments, capable of providing formation evaluation measurements with the same precision and accuracy as the industry's highest quality sensors, at much higher logging speeds. Logging speeds are up to twice the speed of conventional triple-combo and quad combo logging tool strings. Speeds of upto 3600 ft/hr (1080 m/min) are possible. The logging system may include four standard major open hole measurements (resistivity, density, neutron, acoustic) plus auxiliary services.

The resolution and accuracy of logging measurements is determined by the type of measurement and the type of formation being logged. The measurement may be tailored to the type of formation. For example, U.S. Pat. No. 5,309,098 to Coates et al. teaches a method and apparatus in which a variable time-window echo-recording system is used to obtain significant improvements in signal quality and logging speed for NMR measurements. An initial test is performed to provide an assessment of the relaxation qualities of the sample. If the test reveals that the sample is a slow-relaxation rock, then the full time is allocated to measuring echoes. However, if the test reveals that the sample is a fast decay rock, then the echo acquisition time window is reduced. This provides increased efficiency since the system is able to maximize the number of measurements made by optimizing the individual sampling intervals to the particular geologic structure being tested.

Generally, prior art methods have conducted logging at a uniform logging speed. A fixed logging speed is used for the entire logging interval. This flies in the face of logic since reservoir intervals form only a small portion of the entire geologic section and it is only in reservoir intervals is it necessary to get precise and accurate measurements with high resolution: in the non-reservoir intervals, high precision and accuracy are not usually necessary.

It would be desirable to have a method and apparatus of logging a borehole in which the inefficiencies of the prior art are overcome. Such an invention should preferably be able to accommodate a variety of logging tools. The present invention satisfies this need.

SUMMARY OF THE INVENTION

One embodiment of the invention is a method of conducting logging operations of a borehole in an earth formation. A plurality of formation evaluation (FE) sensors are conveyed into the borehole using a conveyance device. The conveyance device is used to move the plurality of FE sensors at a logging speed while making measurements with the FE sensors. An expert system is used for analyzing said measurements made by the FE sensors. A signal for alteration of the logging speed is provided based on the analysis. The sensors may include a resistivity sensor, a natural gamma ray sensor, a porosity sensor, a density sensor, a nuclear magnetic resonance sensor and/or an acoustic sensor. The conveyance device may be a wireline or a slickline. The logging speed may be altered based on the provided signal. In addition, a wait time for NMR signal acquisition, and/or the number of echoes acquired in NMR signal acquisition may be altered. The signal to alter may be based on a determination of a spin relaxation time and/or an identification of a bed boundary.

Another embodiment of the invention is an apparatus for conducting logging operations of a borehole in an earth formation. The apparatus includes a plurality of formation evaluation (FE) sensors, a conveyance which moves the plurality of FE sensors at a logging speed while making measurements with said FE sensors, a processor including an expert system which analyzes the measurements made by the FE sensors, and a processor which provides a signal for alteration of the logging speed based on the analysis. At least one of the processors is at a downhole location. The FE sensors may include a resistivity sensor, a natural gamma ray sensor, a porosity sensor, a density sensor, a nuclear magnetic resonance sensor, and/or an acoustic sensor. The conveyance device may be a wireline or a slickline. The apparatus may further include a device which positions one of the FE sensors at a different distance from the borehole wall than the distance of another of the FE sensors from the borehole wall.

Another embodiment of the invention is a method of conducting logging operations of a borehole in an earth formation in which a nuclear magnetic resonance (NMR) sensor is conveyed into the borehole on a conveyance device. A fraction of at least one sensitive volume of the NMR sensor that includes borehole fluid is determined. The sensitive volume is altered based on the determination.

There may be a plurality of sensitive volumes from which NMR signals are obtained, the determination being based on the NMR signals from the plurality of sensitive volumes. The determination may also be made based on a standoff measurement. Altering the sensitive volume may be done by altering a frequency of operation of the NMR tool, altering a standoff distance of the tool, using a field shifting magnet and/or altering a distance of the sensitive volume from the borehole wall. An additional sensor responsive to a property of the formation may be used and the logging speed altered based on analysis of outputs of the additional sensor and the NMR sensor.

Another embodiment of the invention is an apparatus for conducting logging operations of a borehole in an earth formation. The apparatus includes a conveyance device which conveys a nuclear magnetic resonance (NMR) sensor into the borehole, and a processor. The processor determines a fraction of at least one sensitive volume of the NMR sensor including a borehole fluid, and alters the at least one sensitive volume based on the determination. The NMR sensor may have a plurality of sensitive volumes from which NMR signals are obtained. The processor may make the determination based on the NMR signals from the plurality of sensitive volumes. The processor may alter the sensitive volume by changing a frequency of operation of the NMR sensor and/or by activating a field shifting magnet. The apparatus may include a caliper which determines a standoff of the NMR sensor and the processor may make the determination base don the standoff. The caliper may be an acoustic caliper or a mechanical caliper. The apparatus may include a device that alters the sensitive volume by changing the position of the NMR sensor inside the borehole. The apparatus may include at least one additional formation evaluation sensor and the processor may alter the logging speed based on the outputs of the NMR sensor and the at least one additional sensor.

Another embodiment of the invention is a machine readable medium for use with an apparatus for conducting logging operations of a borehole in an earth formation. The apparatus includes a conveyance device which conveys a nuclear magnetic resonance (NMR) sensor into the borehole. The medium includes instructions which enable determination of a fraction of at least one sensitive volume of the NMR sensor including a borehole fluid and altering the at least one sensitive volume based on the determination. The medium may be a ROM, an EPROM, an EEPROM, a Flash Memory and/or an Optical disk.

BRIEF DESCRIPTION OF THE DRAWINGS

For detailed understanding of the present invention, reference should be made to the following detailed description of the preferred embodiment, taken in conjunction with the accompanying drawing and in which.

DETAILED DESCRIPTION OF THE INVENTION

The present invention is discussed with reference to specific logging instruments that may form part of a string of several logging instruments for conducting wireline logging operations. It is to be understood that the choice of the specific instruments discussed herein is not to be construed as a limitation and that the method of the present invention may also be used with other logging instruments as well.

Figure 1:
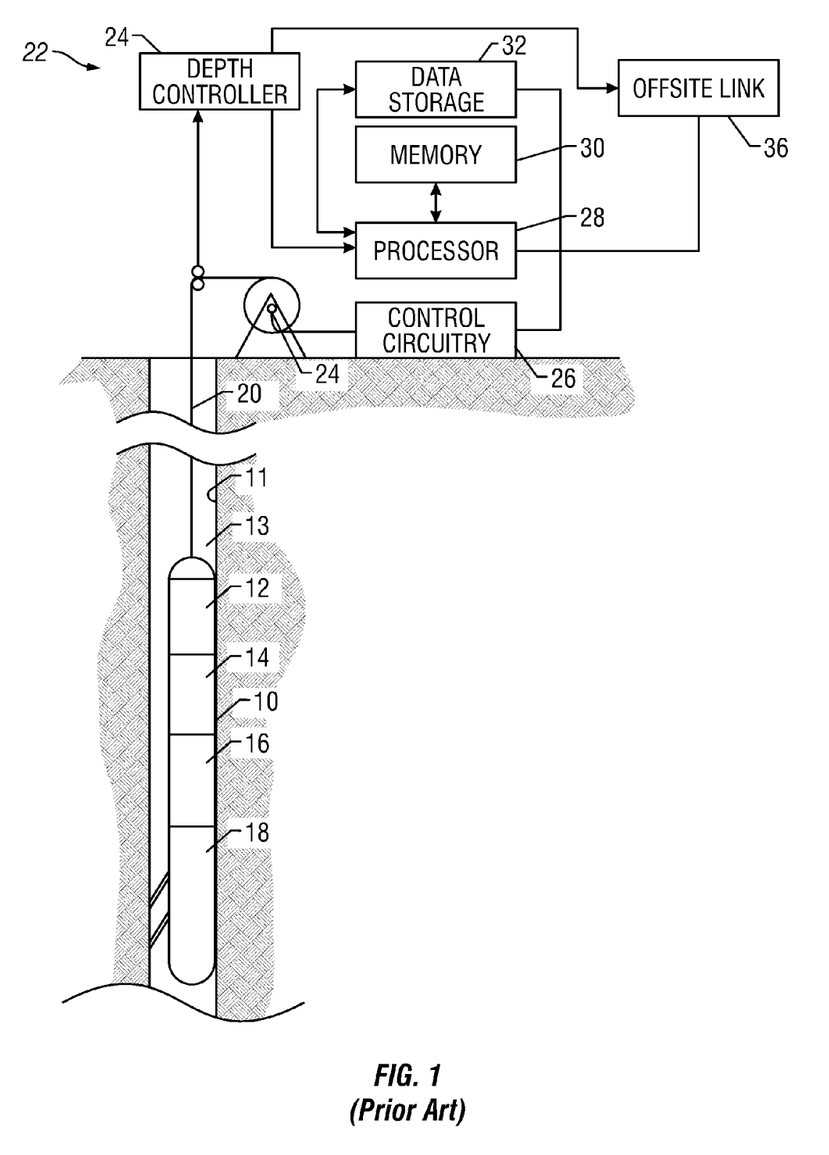
FIG. 1 (prior art) is a schematic illustration of a wireline logging system including a plurality of sensors.

A typical configuration of the logging system is shown in FIG. 1. This is a modification of an arrangement from U.S. Pat. No. 4,953,399 to Fertl et al. having the same assignee as the present invention and the contents of which are incorporated herein by reference. Shown in FIG. 1 is a suite of logging instruments 10, disposed within a borehole 11 penetrating an earth formation 13, illustrated in vertical section, and coupled to equipment at the earth's surface in accordance with the method and apparatus for determining characteristics of clay-bearing formations of the present invention. Logging instrument suite 10 may include a resistivity device 12, a natural gamma ray device 14, and two porosity-determining devices, such as a neutron device 16 and a density device 18. Collectively, these devices and others used in the borehole for logging operations are referred to as formation evaluation sensors. Resistivity device 12 may be one of a number of different types of instruments known to the art for measuring the electrical resistivity of formations surrounding a borehole so long as such device has a relatively deep depth of investigation. For example, a HDIL (High Definition Induction Logging) device such as that described in U.S. Pat. No. 5,452,761 to Beard et al. having the same assignee as the present invention and the contents of which are fully incorporated herein by reference may be used. Natural gamma ray device 14 may be of a type including a scintillation detector including a scintillation crystal cooperatively coupled to a photomultiplier tube such that when the crystal is impinged by gamma rays a succession of electrical pulses is generated, such pulses having a magnitude proportional to the energy of the impinging gamma rays. Neutron device 16 may be one of several types known to the art for using the response characteristics of the formation to neutron radiation to determine formation porosity. Such a device is essentially responsive to the neutron moderating properties of the formation. Density device 18 may be a conventional gamma-gamma density instrument such as that described in U.S. Pat. No. 3,321,625 to Wahl, used to determine the bulk density of the formation. A downhole processor may be provided at a suitable location as part of the instrument suite.

Instrument suite 10 is conveyed within borehole 11 by a cable 20 containing electrical conductors (not illustrated) for communicating electrical signals between instrument suite 10 and the surface electronics, indicated generally at 22, located at the earth's surface. Logging devices 12, 14, 16 and 18 within instrument suite 10 are cooperatively coupled such that electrical signals may be communicated between each device 12, 14, 16 and 18 and surface electronics 22. Cable 20 is attached to a drum 24 at the earth's surface in a manner familiar to the art. Instrument suite 10 is caused to traverse borehole 11 by spooling cable 20 on to or off of drum 24, also in a manner familiar to the art.

Surface electronics 22 may include such electronic circuitry as is necessary to operate devices 12, 14, 16 and 18 within instrument suite 10 and to process the data therefrom. Some of the processing may be done downhole. In particular, the processing needed for making decisions on speeding up (discussed below) for slowing down the logging speed is preferably down downhole. If such processing is done downhole, then telemetry of instructions to speed up or slow down the logging could be carried out substantially in real time. This avoids potential delays that could occur if large quantities of data were to be telemetered uphole for the processing needed to make the decisions to alter the logging speed. It should be noted that with sufficiently fast communication rates, it makes no difference where the decision making is carried out. However, with present data rates available on wirelines, the decision making is preferably done downhole.

Control circuitry 26 contains such power supplies as are required for operation of the chosen embodiments of logging devices within instrument suite 10 and further contains such electronic circuitry as is necessary to process and normalize the signals from such devices 12, 14, 16 and 18 in a conventional manner to yield generally continuous records, or logs, of data pertaining to the formations surrounding borehole 11. These logs may then be electronically stored in data storage 32 prior to further processing. The processor 28 includes the ability, such as that described in U.S. Pat. No. 4,271,356 to Groeschel et al, for separating radiation measurements from natural gamma ray device 14 into individual energy bands centered about energy peaks of selected elemental sources of radiation, preferably the energy peaks of potassium, uranium and thorium. This processing of the natural gamma ray device could also be done by the downhole processor.

Surface electronics 22 may also include such equipment as will facilitate machine implementation of the method of the present invention. Processor 28 may be of various forms but preferably is an appropriate digital computer programmed to process data from logging devices 12, 14, 16 and 18. Memory unit 30 and data storage unit 32 are each of a type to cooperatively interface with processor 28 and/or control circuitry 26. Depth controller 34 determines the longitudinal movement of instrument suite 20 with borehole 11 and communicates a signal representative of such movement to processor 28. The logging speed is altered in accordance with speedup or slowdown signals that may be communicated from the downhole processor, or provided by the surface processor, as discussed below. This is done by altering the rotation speed of the drum 24. Offsite communication may be provided, for example by a satellite link, by the telemetry unit 36.

While running different logging instruments in a single wireline run, the present invention may use a configuration disclosed in U.S. patent application Ser. No. 10/780,167 of Frost et al. filed on Feb. 17, 2004. The teachings of Frost recognize the fact that different logging instruments operate best at different standoffs from the borehole wall.

Figure 2:
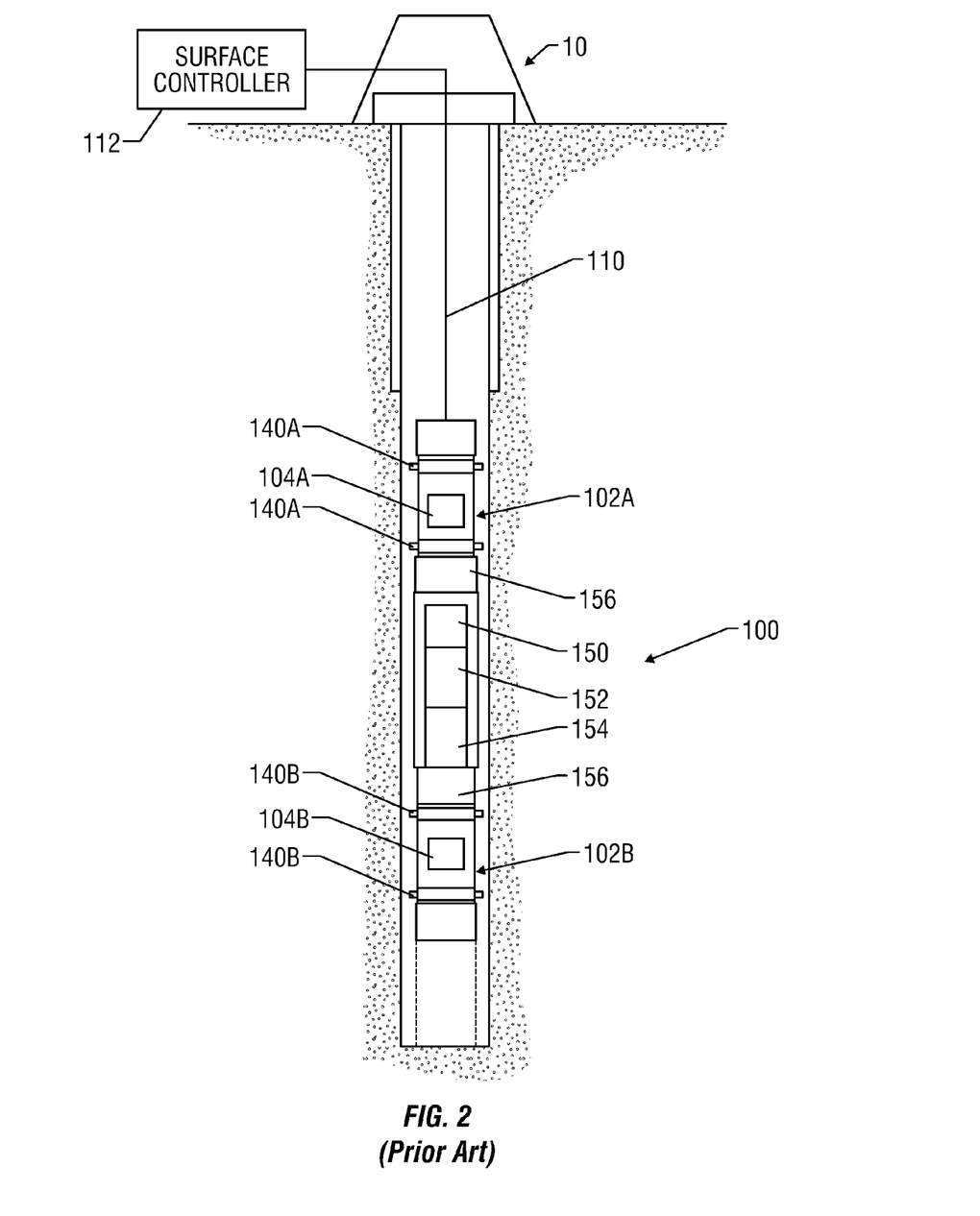
FIG. 2 (prior art) is an embodiment of a system using a radially adjustable module adapted for use in logging operations.

Referring next to FIG. 2, there is shown a rig 10 on the surface that is positioned over a subterranean formation of interest. The rig 10 can be a part of a land or offshore a well production/construction facility. A borehole formed below the rig 10 includes a cased portion 42 and an open hole portion 11. In certain instances (e.g., during drilling, completion, work-over, etc.), a logging operation is conducted to collect information relating to the formation and the borehole. Typically, a tool system 100 is conveyed downhole via a wireline 20 to measure one or more parameters of interest relating to the borehole and/or the formation 13. The term "wireline" as used hereinafter includes a cable, a wireline, as well as a slickline. The tool system 100 can include an instrument suite comprising one or more modules 102a,b, each of which has a tool or a plurality of tools 104a,b, adapted to perform one or more downhole tasks. The term "module" should be understood to be a device such as a sonde or sub that is suited to enclose, house, or otherwise support a device that is to be deployed into a borehole. While two proximally positioned modules 102a,b and two associated tools 104a,b, are shown, it should be understood that a greater or fewer number may be used.

In one embodiment, the tool 104a is a formation evaluation sensor adapted to measure one or more parameters of interest relating to the formation or borehole. It should be understood that the term formation evaluation sensor encompasses measurement devices, sensors, and other like devices that, actively or passively, collect data about the various characteristics of the formation, directional sensors for providing information about the tool orientation and direction of movement, formation testing sensors for providing information about the characteristics of the reservoir fluid and for evaluating the reservoir conditions. The formation evaluation sensors may include resistivity sensors for determining the formation resistivity, dielectric constant and the presence or absence of hydrocarbons, acoustic sensors for determining the acoustic porosity of the formation and the bed boundary in formation, nuclear sensors for determining the formation density, nuclear porosity and certain rock characteristics, nuclear magnetic resonance sensors for determining the porosity and other petrophysical characteristics of the formation. The direction and position sensors preferably include a combination of one or more accelerometers and one or more gyroscopes or magnetometers. The accelerometers preferably provide measurements along three axes. The formation testing sensors collect formation fluid samples and determine the properties of the formation fluid, which include physical properties and chemical properties. Pressure measurements of the formation provide information about the reservoir characteristics.

The tool system 100 can include telemetry equipment 150, a local or downhole controller 152 and a downhole power supply 154. The telemetry equipment 150 provides two-way communication for exchanging data signals between a surface controller 112 and the tool system 100 as well as for transmitting control signals from the surface processor 112 to the tool system 100.

In an exemplary arrangement, and not by way of limitation, a first module 102a includes a tool 104a configured to measure a first parameter of interest and a second module 102b includes a tool 104b that is configured to measure a second parameter of interest that is either the same as or different from the first parameter of interest. In order to execute their assigned tasks, tools 104a and 104b may need to be in different positions. The positions can be with reference to an object such as a borehole, borehole wall, and/or other proximally positioned tooling. Also, the term "position" is meant to encompass a radial position, inclination, and azimuthal orientation. Merely for convenience, the longitudinal axis of the borehole ("borehole axis") will be used as a reference axis to describe the relative radial positioning of the tools 104a,b. Other objects or points can also be used as a reference frame against which movement or position can be described. Moreover, in certain instances, the tasks of the tools 104a,b can change during a borehole-related operation. Generally speaking, tool 104a can be adapted to execute a selected task based on one or more selected factors. These factors can include, but not limited to, depth, time, changes in formation characteristics, and the changes in tasks of other tools.

Modules 102a and 102b may each be provided with positioning devices 140a, 140b, respectively. The positioning device 140 is configured to maintain a module 102 at a selected radial position relative to a reference position (e.g., borehole axis). The position device 140 also adjusts the radial position of module 102 upon receiving a surface command signal and/or automatically in a closed-loop type manner. This selected radial position is maintained or adjusted independently of the radial position(s) of an adjacent downhole device (e.g., measurement tools, sonde, module, sub, or other like equipment). An articulated member, such a flexible joint 156 which couples the module 102 to the tool system 100 provides a degree of bending or pivoting to accommodate the radial positioning differences between adjacent modules and/or other equipment (for example a processor sonde or other equipment). In other embodiments, one or more of the positioning devices has fixed positioning members.

Figure 3:
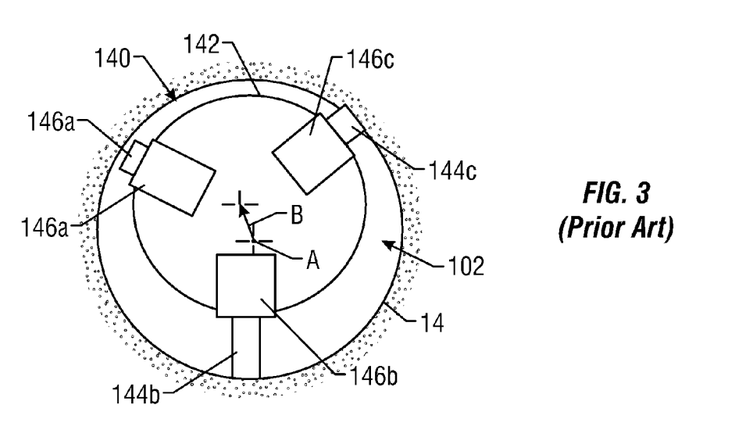
FIG. 3 (prior art) illustrates a sectional view of one embodiment of a positioning device made in accordance with the present invention.

The positioning device 140 may include a body 142 having a plurality of positioning members 144(a,b,c) circumferentially disposed in a space-apart relation around the body 142. The members 144(a,b,c) are adapted to independently move between an extended position and a retracted position. The extended position can be either a fixed distance or an adjustable distance. Suitable positioning members 144 (a,b,c) include ribs, pads, pistons, cams, inflatable bladders or other devices adapted to engage a surface such as a borehole wall or casing interior. In certain embodiments, the positioning members 144(a,b,c) can be configured to temporarily lock or anchor the tool in a fixed position relative to the borehole and/or allow the tool to move along the borehole.

Drive assemblies 146(a,b,c) are used to move the members 144(a,b,c). Exemplary embodiments of drive assemblies 146(a,b,c) include an electro-mechanical system (e.g., an electric motor coupled to a mechanical linkage), a hydraulically-driven system (e.g., a piston-cylinder arrangement fed with pressurized fluid), or other suitable system for moving the members 144(a,b,c) between the extended and retracted positions. The drive assemblies 146(a,b,c) and the members 144(a,b,c) can be configured to provide a fixed or adjustable amount of force against the borehole wall. For instance, in a positioning mode, actuation of the drive assemblies 146(a,b,c) can position the tool in a selected radial alignment or position. The force applied to the borehole wall, however, is not so great as to prevent the tool from being moved along the borehole. In a locking mode, actuation of the drive assembly 146(a,b,c) can produce a sufficiently high frictional force between the members 144(a,b,c) and the borehole wall as to prevent substantial relative movement. In certain embodiments, a biasing member (not shown) can be used to maintain the positioning members 144(a,b,c) in a pre-determined reference position. In one exemplary configuration, the biasing member (not shown) maintains the positioning member 144(a,b,c) in the extended position, which would provide centralized positioning for the module. In this configuration, energizing the drive assembly overcomes the biasing force of the biasing member and moves one or more of the positioning members into a specified radial position, which would provide decentralized positioning for the module. In another exemplary configuration, the biasing member can maintain the positioning members in a retracted state within the housing of the positioning device. It will be seen that such an arrangement will reduce the cross sectional profile of the module and, for example, lower the risk that the module gets stuck in a restriction in the borehole.

The positioning device 140 and drive assembly 146(a,b,c) can be energized by a downhole power supply (e.g., a battery or closed-loop hydraulic fluid supply) or a surface power source that transmits an energy stream (e.g., electricity or pressurized fluid) via a suitable conduit, such as the umbilical 120. Further, while one drive assembly (e.g., drive assembly 146a) is shown paired with one positioning member 144 (e.g., position member 144a), other embodiments can use one drive assembly to move two or more positioning members.

Figure 4:
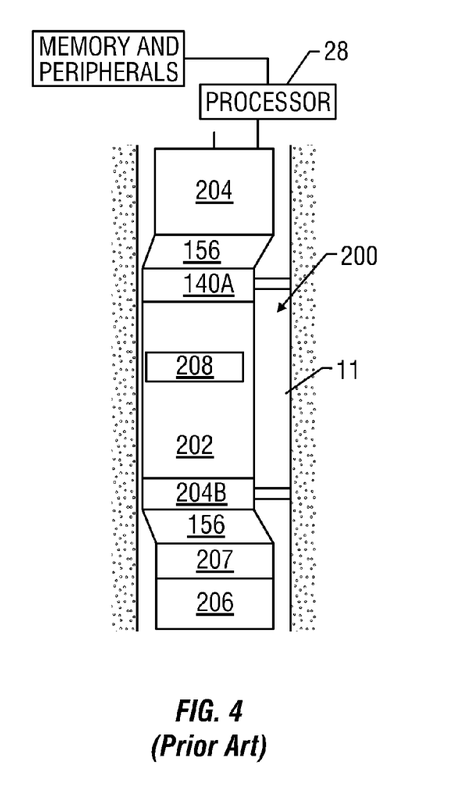
FIG. 4 (prior art) is a schematic elevation view of radially adjustable module positioned in an open hole portion of a borehole.

Referring now to FIG. 4 there is shown an exemplary formation evaluation tool system 200 disposed in an open hole section 11. The tool system 200 includes a plurality of modules or subs for measuring parameters of interest. An exemplary module 202 is shown coupled to an upper tool section 204 and a lower tool section 206 by a flexible member 156. In one exemplary embodiment, the module 202 supports an NMR tool 208. As discussed in U.S. Pat. No. 6,525,535 to Reiderman et al., depending upon the size of the borehole, the NMR tool may be operated in either a centralized manner or in an eccentric manner. In the open hole 18, the acoustic tool 208 may be set in a decentralized position (i.e., radially eccentric position) by actuating the positioning members 140a and 140b. This decentralized or radially offset position is substantially independent of the radial positions of the downhole device (e.g., measurement devices and sensors) along or in the upper/lower tool string section 204 and 206. That is, the upper or tool string section 204 and 206 can have formation evaluation sensors and measurement devices that are in a radial position that is different from that of the module 202. In this decentralized or radially offset position, the NMR tool can be used to gather data in large diameter boreholes. In a small diameter borehole, the NMR tool may be operated in a central position of the borehole. It should be appreciated that such motion can be accomplished by sequentially varying the distance of extension/retraction of the positioning members.

Figure 5:
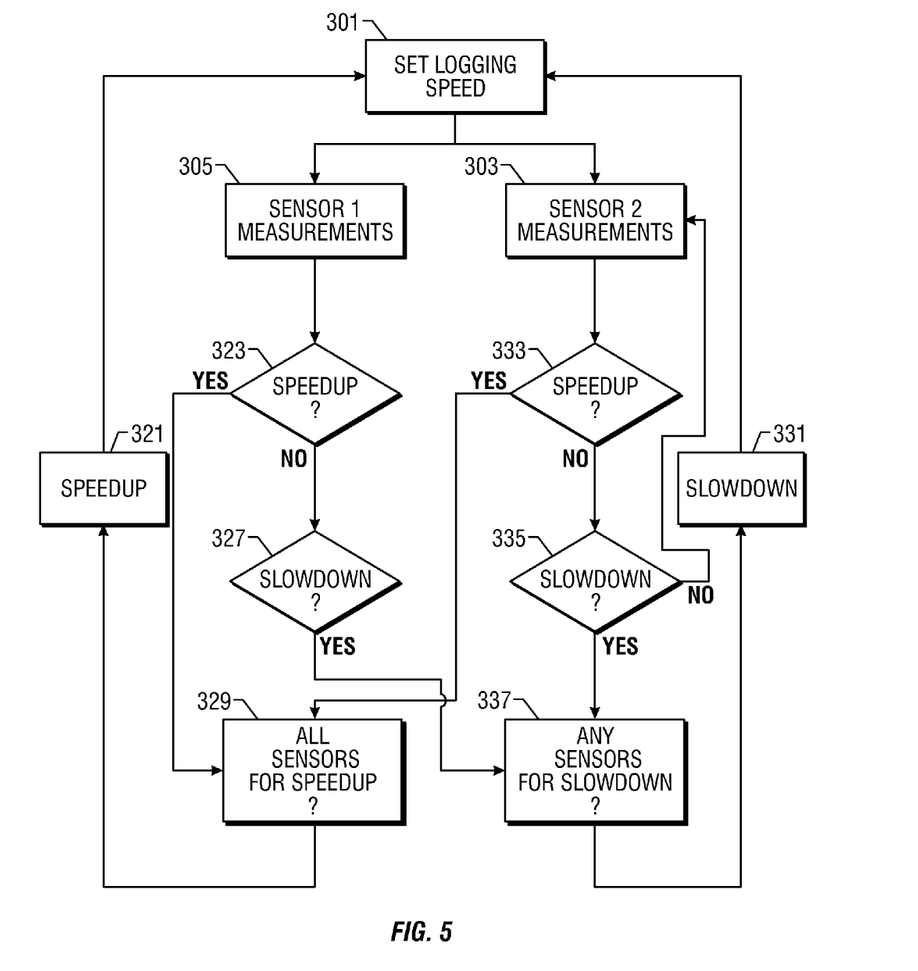
FIG. 5 is a schematic illustration of steps involved in the method of the present invention.

Referring next to FIG. 5, a flow chart generally illustrating the method of the present invention is shown. The downhole tool system is operating at an initial logging speed 301. The initial logging speed may be determined based on prior knowledge of the expected geologic formations and fluids. Measurements are made with a plurality of formation evaluation sensors. To simplify the illustration, only two such FE sensors depicted by 303 and 305 are shown. In actual practice, there may be more than two FE sensors in the logging system. As will be discussed later, the signals measured by the sensor 305 are analyzed by a processor, preferably the downhole processor, to see if the data quality are good enough to permit a speedup 323 of logging. The processing may also be done by a surface processor, or by both a surface processor and a downhole processor. Similarly, the signals measured by sensor 303 are analyzed by a processor to see if the data quality are good enough to permit a speedup 333 of logging. The specific nature of the check is discussed below with reference to individual sensor types. Similarly, the measurements of sensor 303 are checked to see if a speedup is warranted 333. If all the sensors provide a speedup signal 329, a speedup signal is provided 321. Not shown in FIG. 4 is a check to make sure that all the speedup signals are valid. Possible situations in which a speedup signal may not be valid are discussed below.

Checks are also made to see if the sensor 305 would require a slower logging speed 327 with a similar check to see if the sensor 303 would require a slower logging speed 335. The specific nature of the check for slower logging speed is discussed later. If at least one of the sensors provide a valid slowdown signal 337, then logging is slowed down 331. It should further be noted that the order of performing the slowdown and speedup evaluation in FIG. 4 is for illustrative purposes only, and the evaluation could be performed in the opposite order. An important feature of the invention is summarized in the following test:

1. If all the sensors provide a valid speedup signal, then logging speed is increased;
2. If one or more of the sensors provide a valid slowdown signal, then logging speed is decreased; and
3. If neither (1) nor (2) occurs, the logging speed is maintained.

The decision as to whether to speed up or slow down the logging may be based on a comparison measurements made over several time intervals. With the natural gamma ray tool, a typical sampling rate is 10 ms. With a logging speed of 1200 ft/hr, 100 samples are obtained every second, which corresponds to a distance of four inches. If the average and/or the variance of measurements over say 1 second is substantially the same as the average of measurements over 2 seconds, it is an indication that logging speed may be increased without loss of resolution of loss of precision. With the HDIL tool, for example, transmitter and receiver coils are configured to operate with different depths of investigation by operating at several frequencies and/or by using data from several transmitter-receiver spacings. There is a high degree of redundancy in the data. Again, by comparing averages over different time intervals, an indication can be obtained as to whether logging speed may be increased, or, conversely, whether logging speed should be decreased.

With nuclear sensors such as used for neutron porosity or gamma ray density logs, the count rates are subject to statistical fluctuations. This is due to the fact that over short time intervals, the source emits radiation that may fluctuate, and furthermore, the interaction of the source radiation with nuclei in the formation is also governed by statistical processes. In order to make a meaningful determination of porosity and/or density, it becomes important to make sure that the actual number of accumulated counts has a minimum value for all the detectors used in making the nuclear measurements.

Another point to note with respect to nuclear sensors is that some compensation is applied to account for offset of the detectors from the borehole wall. For example, if $\rho_{ss}$ and $\rho_{ls}$ are measurements made by short spaced (SS) and long spaced (LS) sensors, a density correction is applied to give a corrected density according to the relation:

$$\Delta\rho = \rho - \rho_{LS} = f(\rho_{LS} - \rho_{SS}) \qquad (1)$$

This is called the "spine and rib" correction. In situations where there are washouts, is possible that the individual sensor measurements may pass the tests described above regarding the count rate and the statistical fluctuations. Nevertheless, a corrected density measurements may still be invalid due to the large washout. This is an example of the requirement that the speedup or slowdown indicator (discussed above) be a valid one.

An acoustic sensor may also be part of the instrument suite. This is generally used at least for measurements of compressional (P-wave) velocities of earth formations. To make measurements of P-wave velocities, the transmitter(s) and receivers that comprise the acoustic sensor are operated in a monopole mode. Energy generated by the transmitter travels through the formation as a refracted P-wave and from traveltime measurements at the array of receivers, the P-wave velocity can be determined. The semblance of the received signal is an indication of the quality of the data, and if the semblance is sufficiently high, then it is possible to increase the logging speed without detriment. It should be noted that if the formation shear wave (S-wave) velocity is greater than the velocity of sound in the drilling mud, it is possible to determine formation S-velocities using a monopole excitation.

The acoustic tool may also be operated in a dipole mode in which shear waves (S-waves) are excited in the formation. Again, the semblance of the received signals may be used as an indicator for possible speedup of logging speed. It should be noted that acoustic measurements take several milliseconds to make, compared to the few microseconds needed for nuclear and resistivity measurements. The acoustic tool may also be operated in the so-called cross-dipole mode wherein the transmitter is activated in a first dipole mode and then activated in a second dipole mode orthogonal to the first dipole mode. The cross-dipole mode is useful in determining azimuthal anisotropy in the earth formation, an indication of possible fracturing. It should be clear that with respect to the acoustic tool, the speedup or slowdown indicator is based on all of the modes of acquisition that are desired.

For logging in laminated reservoirs (that have transverse isotropy in both resistivity and acoustic properties), a multicomponent resistivity sensor may be included in the instrument suite. Service with such a sensor is provided by Baker Hughes Incorporated under the mark 3DEX$^{SM}$ and a tool suitable for the purpose is disclosed in U.S. Pat. No. 6,147,496 to Strack et al. Using such a device, it is possible to determine resistivity anisotropy in the earth formation that is a better indication of reservoir quality than the HDIL measurements (that are sensitive only to horizontal resistivity). In anisotropic reservoirs, it may also be desirable to operate the acoustic sensor in the dipole mode. The natural gamma ray sensors do not necessarily have the resolution to be able to identify laminations at the scale at which resistivty and/or acoustic anisotropy may occur. Consequently, it may be desirable to include a high resolution resistivity sensor, such as a microlaterolog, as part of the instrument suite. Signals from such a sensor could be used to start acquisition with the 3DEX device and/or to switch the acoustic sensor to joint monopole/dipole operation.

In one embodiment of the invention, a processor including an expert system analyzes the output of the FE sensors. The processor that does the analysis may be a downhole processor or a surface processor. The expert system determines the lithology of the formation being logged and a speedup or slowdown signal may be provided based on the determine lithology. For example, in shale formations where high resolution and detailed NMR spin relaxation information is not necessary and the NMR spin-lattice relaxation time is short, a speedup signal may be provided. If a microresistivity log indicates a laminated formation, a slowdown signal may be provided to enable accurate 3DEX measurements.

U.S. patent application Ser. No. 10/828,812 of Kruspe et al. having the same assignee as the present application and the contents of which are fully incorporated herein by reference, discloses the use of an expert system as part of a processor that uses the output of FE sensors to determine lithology.

Specifically, gamma rays measurements may be used to determine the shale content of the formation at the depth of the NMR sensors. In a shaly interval, short pulse sequences and small values of □TE are sufficient. The presence of hydrocarbons in the formation is diagnosed from resistivity measurements. The presence of gas in the formation may be indicated by acoustic log measurements. As would be known to those versed in the art, even a small amount of gas in the formation significantly lowers the P-wave velocity in a porous sand formation and additional changes in P-wave velocity changes are only slightly affected by the amount of gas present. In such a situation, it is desirable to use a dual wait time acquisition and processing to determine the gas saturation.

The Expert System is preferably implemented using neural networks (NNs). In one embodiment of the invention, more than one NN is used. A first NN is used for determination of lithology and formation fluid type from FE measurements. A second NN may be used for modifying the acquisition and processing parameters based upon the knowledge of the lithology and fluid type and the drilling conditions.

In one embodiment of the present invention, acquisition of data using an NMR tool is dynamically altered. U.S. Pat. No. 5,309,098 to Coates teaches an arrangement in which an initial test is performed to determine the relaxation characteristics of the formation being tested. This information obtained from this initial test is then used to select a sampling interval which optimizes the collection of data for the particular pore structure of the formation being tested. The NMR tool disclosed in Coates is a single frequency tool such as that described in U.S. Pat. No. 3,213,357 to Brown et al.

One of the problems with NMR tools is the possibility of the sensitive volume extending into the borehole. In such a situation, the NMR signals from the borehole fluid will dominate the signals from the formation, rendering the results incorrect. In one embodiment of the present invention, a test is performed at intervals that may be determined in many ways. For example, standoff measurements made by a caliper may be used to detect washouts. From the standoff measurements, U.S. Pat. No. 6,603,310 to Georgi et al., having the same assignee as the present application and the contents of which are fully incorporated herein by reference, teaches the determination of the fraction of the sensitive volume that includes borehole fluid and correcting the NMR signals for the contamination. In the present invention, the sensitive volume is altered on the basis of the standoff measurements. This may be done in many ways.

Figure 6A:
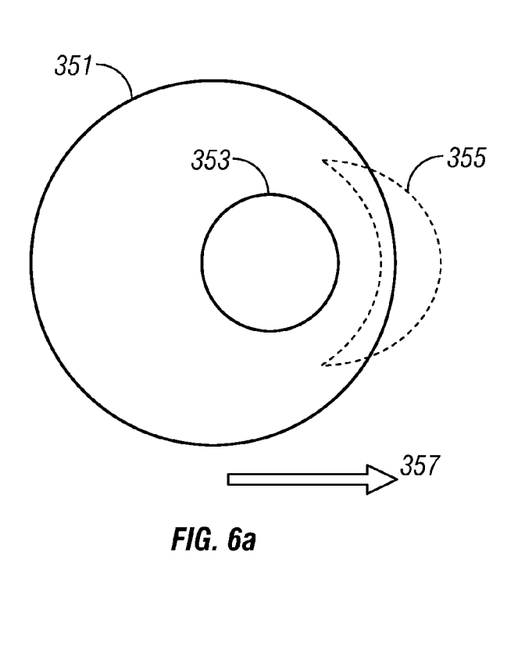
FIGS. 6a and 6b show the alteration of the sensitive volume by movement of the tool within the borehole.
Figure 6B:
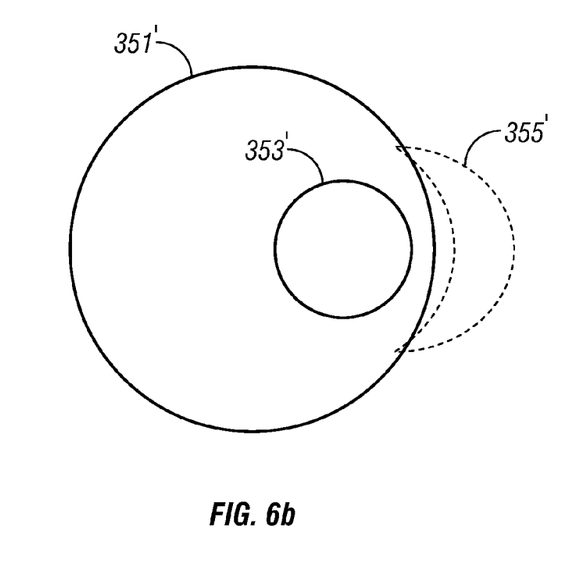

In one embodiment of the invention, the NMR tool may be used as part of the logging string of Frost discussed above with reference to FIGS. 2 and 4. The standoff measurements may then be used by a processor to control the movement of an eccentered tool towards or away from the borehole wall. This is illustrated with reference to FIGS. 6a and 6b. Shown in FIG. 6a is a borehole 351 with a logging tool denoted by 353 inside it. The sensitive volume is denoted by 355. The direction of the static magnetic field is given by 357. For the case shown in FIG. 6a, the sensitive volume extends into the borehole. By moving the tool to the position indicated by 353' in FIG. 6b, the sensitive volume 355' is completely within the formation.

Figure 7A:
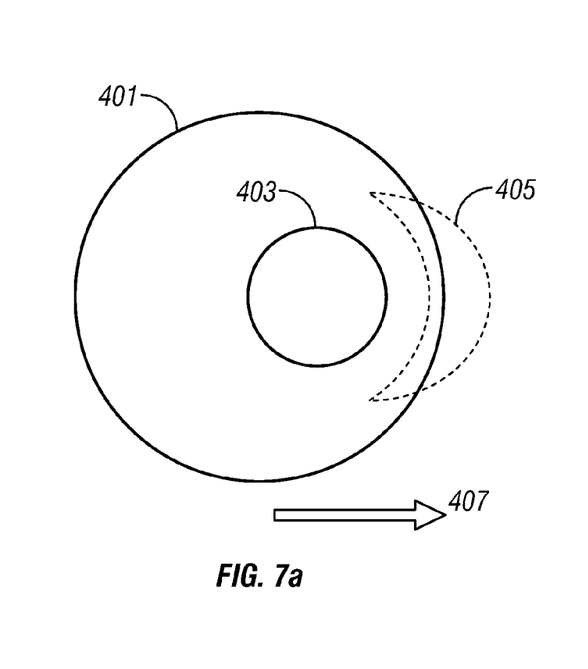
FIGS. 7a and 7b show alteration of the sensitive volume by use of a field shifting magnet and/or altering the frequency of operation.

In another embodiment of the invention, a field shifting electromagnet may be used to alter the distance from the tool for a given frequency of operation. When the field of the field-shifting magnet reinforces the static magnetic field of the permanent magnet, then for a given frequency of operation, the sensitive region is moved away from the tool. When the field of the field-shifting magnet opposes the static magnetic field of the permanent magnet, then for a given frequency of operation, the sensitive region is moved closer to the tool. Shown in FIG. 7a is a case where the sensitive region 405 of the tool 403 extends into the borehole 401. The direction of the static magnetic field is given by 407. By increasing the static magnetic field strength using the field shifting magnet, the sensitive volume 405' in FIG. 7b does not extend into the borehole 401' for the same position of the tool 403'.

Figure 7B:
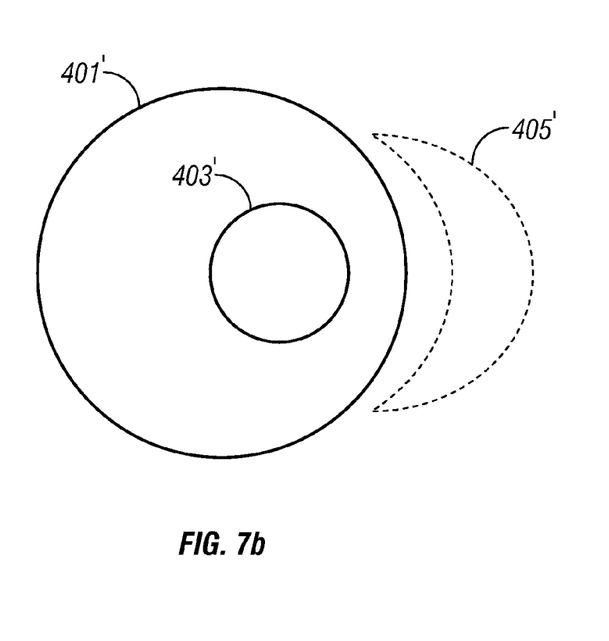

Instead of using a field shifting magnet, the sensitive region can be changed by altering the frequency of operation. Lowering the frequency moves the sensitive region away from the tool while increasing the frequency moves the sensitive region towards the tool. The principle for this is the same as for the field shifting magnet shown in FIGS. 7a and 7b. It should be noted that the example shown in FIGS. 7a and 7b are for an eccentered tool having an arcuate region of examination. This is not a limitation of the invention and the method could also be used for a centered tool within the borehole.

The discussion above with reference to FIGS. 6a, 6b, 7a and 7b dealt with a examples in which a single sensitive region was altered. The method of dynamic alteration of the region of examination may also be used with a multifrequency logging tool such as that disclosed in Reiderman. U.S. patent application Ser. No. 10/855,230 of Chen et al. having the same assignee as the present invention and the contents of which are incorporated herein by reference discloses a method for determining the fraction of each of a plurality of sensitive volumes that may be affected by the presence of borehole fluid. This may be done without the use of standoff measurements. Chen also teaches a method of correcting the data to correct for the effects of borehole fluids. In the present invention, instead of correcting the data, alteration of the plurality of sensitive volumes may be done using the methods discussed above. Alternatively, data from some of the sensitive volumes may be discarded.

The processing of the measurements made in wireline applications may be done by the surface processor, the downhole processor or a remote location. The data acquisition may be controlled at least in part by the downhole electronics. Implicit in the control and processing of the data is the use of a computer program on a suitable machine readable medium that enables the processors to perform the control and processing. The machine readable medium may include ROMs, EPROMs, EEPROMs, Flash Memories and Optical disks.

As would be known to those versed in the art, wireline logging operations are typically conducted with the instrument suite being pulled up the borehole. This is preferable to logging with the instrument suite being lowered into the borehole since in the latter situation, there may be sticking of the instrument suite into the borehole with the result that the logging depth as determined at the surface location may not correspond to the actual depth of the instruments. With the variations in logging speed that are possible during practice of the present invention, due to the elasticity of the wireline, there may be "yo-yoing" of the instrument suite at the bottom of the wireline. U.S. Pat. Nos. 6,154,704 and 6,256,587 to Jericevic et al., having the same assignee as the present application and the contents of which are fully incorporated herein by reference, present methods for correcting the measurements for the effects of the yo-yoing. In the context of the present invention, this correction may be made after the logging operations are conducted on the stored data at the surface. Alternatively, a correction may be applied downhole prior to any determination to speed up or slow down logging speed.

The present invention has been described in the context of a wireline device. The method of the present invention is equally applicable on slickline conveyed device wherein a downhole processor is used for providing a signal to speed up or slow down the speed. The slickline may optionally be conveyed inside a drilling tubular. The FE sensor measurements are stored in a downhole memory for subsequent retrieval.

While the foregoing disclosure is directed to the preferred embodiments of the invention, various modifications will be apparent to those skilled in the art. It is intended that all variations within the scope of the appended claims be embraced by the foregoing disclosure.

What is claimed is:

1. A method of conducting logging operations of a borehole in an earth formation, the method comprising:
   (a) making measurements using a nuclear magnetic resonance (NMR) sensor in the borehole;
   (b) determining, from the measurements, a fraction of at least one sensitive volume of the NMR sensor that includes a borehole fluid; and
   (c) altering the at least one sensitive volume based on the determination.

2. The method of claim 1 wherein the at least one sensitive volume comprises a plurality of sensitive volumes, the method further comprising:
   (i) obtaining NMR signals from the plurality of sensitive volumes; and
   (ii) making the determination based on the NMR signals from the plurality of sensitive volumes.

3. The method of claim 1 wherein the determination is based at least in part on measurements of a standoff of the sensor from a wall of the borehole.

4. The method of claim 1 wherein altering the at least one sensitive volume further comprises at least one of:
   (i) altering a frequency of operation of the NMR sensor;
   (ii) altering a distance of the NMR sensor from a wall of the borehole;
   (iii) using a field shifting magnet to alter a static magnetic field produced by the NMR sensor; and
   (iv) altering a distance of the at least one sensitive volume from a wall of the borehole.

5. The method of claim 1 further comprising:
   (i) conveying at least one additional sensor into the borehole with the NMR sensor, the at least one additional sensor responsive to a property of the formation;
   (ii) analyzing outputs of the NMR sensor and the at least one additional sensor; and
   (iii) altering a logging speed based on results of the analysis.

6. An apparatus for conducting logging operations of a borehole in an earth formation, the apparatus comprising:
   (a) a nuclear magnetic resonance (NMR) sensor which-makes configured to make measurements within the borehole; and
   (b) a processor configured to:
      (A) determine from the measurements a fraction of at least one sensitive volume of the NMR sensor including a borehole fluid; and
      (B) alter the at least one sensitive volume based on the determination.

7. The apparatus of claim 6 further comprising a device which configured to alter the sensitive volume by changing a position of the NMR sensor relative to a wall of the borehole.

8. The apparatus of claim 6 further comprising at least one additional sensor conveyed into the borehole with the NMR sensor, the at least one additional sensor responsive to a property of the formation; wherein the processor is further configured to:
   (i) analyze outputs of the NMR sensor and the at least one additional sensor; and
   (ii) alter a logging speed based on results of the analysis.

9. The apparatus of claim 6 wherein:
   (i) the at least one sensitive volume comprises a plurality of sensitive volumes,
   (ii) the NMR sensor is configured to obtain NMR signals from the plurality of sensitive volumes; and
   (iii) the processor is configured to make the determination based at least in part on the NMR signals from the plurality of sensitive volumes.

10. The apparatus of claim 9 wherein the processor is further configure to alter the at least one sensitive volume by at least one of:
    (I) changing a frequency of operation of the NMR sensor, and
    (II) activating a field shifting magnet on the NMR sensor.

11. The apparatus of claim 6 further comprising a caliper configured to make a measurement of a standoff of the NMR sensor from a wall of the borehole and wherein the processor is configured to make the determination at least in part on measurements made by the caliper.

12. The apparatus of claim 11 wherein the caliper is selected from the group consisting of (i) an acoustic caliper, and (ii) a mechanical caliper.

13. A machine readable medium for use with an apparatus for conducting logging operations of a borehole in an earth formation, the apparatus comprising:
    (a) a nuclear magnetic resonance (NMR) sensor configured to make measurements within the borehole;
    the medium comprising instructions which enable a processor to:
    (b) determine a fraction of at least one sensitive volume of the NMR sensor including a borehole fluid; and
    (c) alter the at least one sensitive volume based on the determination.

14. The medium of claim 13 wherein the medium is selected from the group consisting of (i) a ROM, (ii) an EPROM, (iii) an EEPROM, (iv) a Flash Memory, and (v) an Optical disk.

* * * * *